US00PP09375P

United States Patent [19]

Bennett

[11] Patent Number: Plant 9,375

[45] Date of Patent: Nov. 21, 1995

[54] MINIATURE ROSE PLANT NAMED 'X-RATED'

[76] Inventors: Cecilia L. D. Bennett, deceased, late of Chula Vista; Susan M. O'Brien, special administrator, 489 Minot Ave., Chula Vista, both of Calif. 91910

[21] Appl. No.: 364,680

[22] Filed: Dec. 22, 1994

[51] Int. Cl.[6] ..... A01H 5/00

[52] U.S. Cl. ..... Plt./7.1

[58] Field of Search ..... Plt./7.1, 8.2, 9

[56] References Cited

U.S. PATENT DOCUMENTS

P.P. 6,843 6/1989 Berg ..... Plt./7.1

*Primary Examiner*—Howard J. Locker

[57] ABSTRACT

The subject of the present disclosure is a new and distinct variety of miniature rose plant, named 'X-Rated', which is characterized by buds and blooms in shades of creamy-white with a blush of pink on the outermost petals. Blooms of this rose are of hybrid tea form and are borne singly and in sprays of 3 to 5 or more. The plant is bushy, vigorous, well-branched, and produces moderate to heavy blooms.

1 Drawing Sheet

The present invention relates to a new and distinct variety of a hardy, dwarf, bush plant of the miniature rose class; the variety being primarily characterized as pink blend.

The variety is further characterized by:

Long stemmed blooms of hybrid tea-type form, borne usually one to a stem but sometimes in compact sprays of 3 to 5 or more. The blooms are held very erect and well above the foliage.

The plant ranges in height from 18 to 24 inches (45 to 60 cm). The canes are sturdy and erect with moderate branching and medium to heavy foliage covering. The plant is a heavy bloomer that does well either in the greenhouse or outdoors.

The plant has good growth habits, and is well-shaped and attractive. The plant bars numerous leaflets of average size. Asexual reproduction of the new variety by cuttings derived from the plant stem, as performed at Chula Vista, Calif., shows that the foregoing and all other characteristics and distinctions come true to form and are established and transmitted through succeeding propagations.

The seed parent was 'Tiki' (hybridized and introduced by McGredy), and the pollen parent was 'Baby Katie' (U.S. Plant Pat. No. 4,471). The plant differs from its seed parent in at least the following ways: It is a miniature rose plant of the pink blend class, and 'Tiki' is a floribunda in the light pink class. The plant differs from its pollen parent in at least the following ways: It produces blooms in shades of creamy-white with a pink blush on the outermost petals, while 'Baby Katie' produces blooms in pale yellow with a blush of salmon.

The single color photographic view shows, in plain view, a bouquet of 'X-Rated' in various stages of maturity from bud stage to nearly open bloom stage.

The descriptive matter which follows pertains to roses grown and color values observed in plants and newly opened blooms in the months of March through November of 1994. The plants were grown outdoors in Chula Vista, Calif., and are believed to be accurate standards for this cultivar in similar conditions of soil and climate elsewhere.

Referring now specifically to the new and distinct variety of miniature rose plant named 'X-Rated', the following is a detailed description thereof in outline; all major color plate identifications being by reference to the British Colour Council Horticultural Chart, except where common terms of color definition are employed.

Type: Hardy, dwarf, bushy, greenhouse or outdoor, exhibition or garden decorative potted plant.

Class: Miniature.

Variety name: 'X-Rated'.

Flowers borne: Usually one to a stem, but occasionally in sprays of 3 to 5 or more on erect stems with foliage well below the blooms.

Quantity of bloom: Heavy both outdoors or greenhouse grown.

Bud:

*Peduncle.*—Average length (30 to 50 mm); of average diameter and average sturdiness; ranging in color from near Scheeles Green (860/3 to 860/1, page 176) with occasional tinting of bronze.

*Hairs.*—Extremely small and sparse with a reddish color; located over the surface of the peduncle and calyx tube.

*Calyx.*—Color range is same as peduncle.

*Opening.*—Opens well in all weather.

*Sepals.*—Permanent; simple and glabrous; spear-shaped; open as the bloom opens, recurving against the peduncle when the bloom is fully opened. Occasional foliaceous appendages attractively supplement sepal terminals; these are of varying lengths.

Bloom:

*Size when fully open.*—Average for a miniature variety (40 to 50 mm).

*Petalage.*—Full — 25 to 35 petals, arranged regularly, plus 5 to 10 petaloids.

*Form.*—Urn-shaped to ovoid as the bloom opens. The petals remain somewhat cupped with the apex and/or margins reflexed outward, becoming at maturity more loosely cupped.

Petals: Fairly thick with good substance; both the upper and under surfaces of all petals have a matte finish.

*Shape.*—Outer petals are of a broad obovate form. The intermediate petals are very much like the outer petals, but narrower. The inner petals are a broad lanceolate form. The petaloids are also lanceolate with come occasional irregularities.

Color: Newly opened flowers from plants grown outdoors (March through November of 1994), Chula Vista, Calif.

*Inner petals.*—Upper and under surfaces — Ranging from near white to near Naples Yellow (403/3 to 403/1, page 121).

*Outer petals.*—Upper surfaces — Ranging from near white to near Napels Yellow (403/3 to 403/1, page 121) at the base with a blush on the outer margins which ranges from near Shell Pink (516/3 to 516/1, page 135) to near Neyron Rose (623/3 to 623, page 76). Pink blush is deeper on blooms grown in warmer/sunny locations and paler on blooms grown in cooler climates or during overcast/cloudy days. Under surfaces — Ranging from near white to near Naples Yellow (403/3 to 403/1, page 121) with only occasional blush of near Neyron Rose (623/3 to 623/2, page 76) on the outermost petals.

*General color effect.*—Newly opened flowers — Creamy white with a pale pink blush on the outer most petals. Three to five days open — Fading to cream to pure white as petals open with a deeper pink blush on the outermost petals. After five days — Pure white inner petals with deeper pink blush on the outer margins of the outermost petals.

Flower longevity: (March through November 1994) Plant in pot 5 to 7 days from bud with sepals reflexed to fully open bloom. Holding at fully opened for 5 to 7 days longer. Cut blooms at living room temperature last 10 to 14 days or longer.

Reproductive organs:

*Stamens.*—A generous amount arranged uniformly around the pistil.

*Filaments.*—Varying in length with shorter filaments more proximal to the pistil; pale yellow in color with anthers of golden yellow.

*Pollen.*—Abundant.

*Pistil.*—Short, spreading and abundant; pale yellow in color.

*Ovaries.*—All encased in calyx.

Hips: Some present; 3 to 5 seeds in each hip.

Foliage:

*Leaves.*—5 to 7 leaflets on average; medium size for a miniature rose plant.

*Leaflets.*—Broad ovate-shaped.

*Margins.*—Very serrated with tinting of bronze, especially noticeable on new foliage.

*Color.*—Ranging from near Spinach Green (0960/3 to 0960, page 187) to near Scheeles Green (860/1 to 860, page 175) with occasional bronzing of the margins, especially on the newer foliage. Upper surfaces have a semi-glossy finish, and the under surfaces have a matte finish of a slightly lighter shade than the upper surfaces.

*Rachis.*—Medium strength; upper surface is grooved with very small hairs over the length of it. Under surface has few (if any) hairs but does have 2 to 5 small thorns.

*Stipules.*—Varying in length from small to medium; average width; tapering auricles angled outward at about 45 degrees.

Growth:

*Habit.*—Dwarf, bushy; above average for a miniature rose plant.

*Character.*—Vigorous; well-branched.

*Canes.*—Medium diameter; sturdy; held erect.

*Main stems and branches.*—Coloration ranges the same as that of the foliage.

*Thorns.*—Averaging less than 5 to 10 per 10 cm on the main stems and branches. Reddish in color; of average size; slender and hooked slightly downward.

The miniature rose plant and its flowers as herein described may vary in slight detail due to climate, soil, and cultural conditions under which the variety may be grown; the present description being of the variety as grown in Chula Vista, Calif.

No information related to insect, disease, or frost tolerance is available due to the controlled growing conditions under which our plants are produced and maintained. These include regular application of fungicides and pesticides on all plants and the immediate elimination of any inferior seedlings. As to frost tolerance, all of our plants are grown in Chula Vista, Calif. which is located in a moderate temperature zone that would rarely experience frost or freezing temperatures.

The following is claimed:

1. A new and distinct variety of miniature rose plant substantially as herein described and illustrated named 'X-Rated'; the plant being characterized by its hardy, dwarf, vigorous growth; by its well branched and attractive appearance; by its hybrid tea form blooms which range from creamy white to near Naples Yellow with a pink blush on the outermost petals of near Shell Pink to near Neyron Rose; and by its relative abundance of blooms, which are usually borne one to a stem but occasionally in sprays of 3 to 5 or more with the blooms held very erect and well above the foliage.

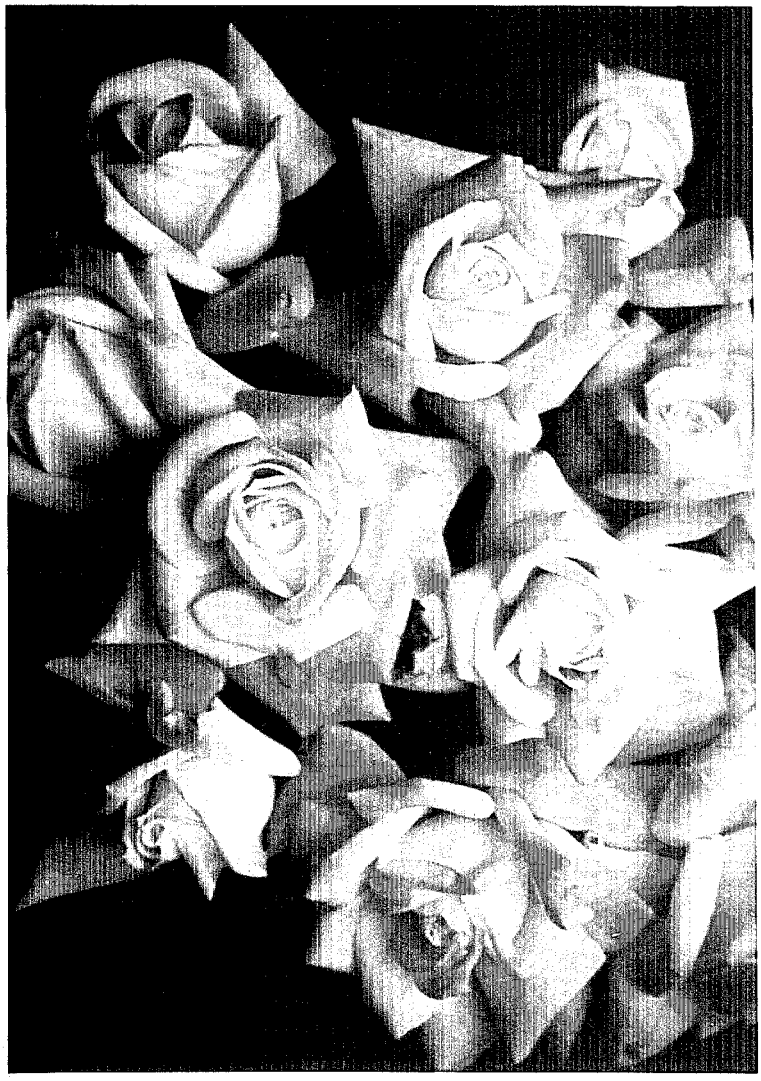

* * * * *